(12) United States Patent
George et al.

(10) Patent No.: US 11,674,119 B2
(45) Date of Patent: Jun. 13, 2023

(54) SPORE-CONTAINING PROBIOTIC COMPOSITIONS AND METHODS

(71) Applicant: Kerry Group Services International Limited, Tralee (IE)

(72) Inventors: Benjamin George, East Troy, WI (US); Howard Cash, Mentor, OH (US); Joseph M. Bradley, Solon, OH (US); Nusair Imam, Monona, IL (US); Stephen G. Cobbe, Madison, WI (US); Eileen O'Shea, Shaker Heights, OH (US)

(73) Assignee: Kerry Group Services International Limited, Tralee (IE)

( * ) Notice: Subject to any disclaimer, the term of this patent is extended or adjusted under 35 U.S.C. 154(b) by 0 days.

(21) Appl. No.: 16/856,540

(22) Filed: Apr. 23, 2020

(65) Prior Publication Data
US 2020/0339942 A1    Oct. 29, 2020

Related U.S. Application Data

(60) Provisional application No. 62/837,589, filed on Apr. 23, 2019.

(51) Int. Cl.
| | | |
|---|---|---|
| *C12N 1/20* | (2006.01) | |
| *A23L 33/135* | (2016.01) | |
| *A23L 2/52* | (2006.01) | |
| *C12R 1/07* | (2006.01) | |

(52) U.S. Cl.
CPC ............ *C12N 1/20* (2013.01); *A23L 2/52* (2013.01); *A23L 33/135* (2016.08); *C12N 1/205* (2021.05); *A23V 2002/00* (2013.01); *C12R 2001/07* (2021.05)

(58) Field of Classification Search
CPC ....................................................... C12N 1/20
See application file for complete search history.

(56) References Cited

U.S. PATENT DOCUMENTS

| | | | |
|---|---|---|---|
| 2015/0118203 A1* | 4/2015 | Boyette | A01K 7/00 119/51.01 |
| 2019/0022153 A1* | 1/2019 | Mehta | A23L 33/135 |

* cited by examiner

*Primary Examiner* — Albert M Navarro
(74) *Attorney, Agent, or Firm* — Sughrue Mion, PLLC

(57) ABSTRACT

A method for preparing a shelf stable spore-containing probiotic alimentary additive is disclosed, the method including providing a liquid slurry including spores from at least one spore-forming probiotic bacterial strain, a saccharide, and a humectant; and pasteurizing the liquid slurry to yield the alimentary additive. The alimentary additive may have a water activity (Aw) of less than about 0.7. The alimentary additive may have a pH from about 2.0 to 9.5. A plurality of the spores may remain in an un-germinated state and uniformly suspended for at least two months after the pasteurizing to yield a shelf stable spore-containing probiotic alimentary additive.

17 Claims, No Drawings

SPORE-CONTAINING PROBIOTIC COMPOSITIONS AND METHODS

CROSS REFERENCE TO RELATED APPLICATIONS

This application claims benefit under 35 U.S.C. § 119(e) to U.S. Provisional Application No. 62/837,589 filed Apr. 23, 2019, the entire contents of which is hereby incorporated by reference in its entirety.

FIELD

Spore-containing probiotic compositions and methods are provided.

BACKGROUND

Probiotic microorganisms when consumed in adequate amounts can confer a health effect on the host. Probiotics today find applications in diverse fields such as food, meal replacements, dietary supplements, nutraceuticals, over the counter drugs as well as prescription drugs. Probiotic products include dairy products and probiotic-fortified food. The products generally require storage at low temperatures to maintain the probiotic activity. Growth of probiotic microorganisms in these products can give rise to offensive odor to the products.

Many probiotic formulations are provided as solid oral dosage forms. While liquid formulations can facilitate ease of application in food and beverage processing applications, to date such formulations do not exist due to the drawbacks associated with liquid probiotic formulations, e.g., achieving a uniform suspension to enable dosage accuracy while maintaining the shelf-life stability of the formulation. Liquid probiotic formulations typically include sugars that can act as substrates and can enhance the risk of undesired metabolite production. Gas producing probiotics can result in bulging of the containers and production of offensive odors and taste. Furthermore, metabolite production can result in death of the probiotic strain and lower viable counts of the probiotic. As a result, such liquid probiotic formulations need to be stored in cold conditions (e.g., 2° C. to 8° C.), which can limit their use in food applications and increase distribution costs.

There are several commercially available liquid probiotic formulations that are available as Health Supplements. For example, "Enterogermina" produced and marketed by Sanofi is a liquid oral suspension that contains 4 strains of *Bacillus clausii*, a species distinct from *Bacillus coagulans*, in purified water at a concentration of 2 billion CFU/5 mL. Enterogermina is specifically recommended for use by people with diarrhea. "Bacilliq SC" is also produced and marketed by Synergia Life Sciences Pvt. Ltd. and does not require cold chain storage. Bacilliq SC contains distinct probiotics strains, *Bacillus subtilis* HU58 and *Bacillus coagulans* SC208, and sugar.

In addition, a conventional probiotic composition is disclosed in U.S. Patent Application Publication No. 2015/0118203 by NCH Corporation ("the '203 publication"). The '203 publication discloses a system for delivering probiotic compositions by gravity feed or non-contact pump to a point of consumption by a plant or animal. The probiotic compositions comprise one or more species of bacteria in spore form, a thickener, one or more acids or salts of acids and optionally a water activity reducer.

There is no consideration in the '203 publication for human consumption of its probiotic composition. Further, the '203 publication has disadvantages in repeatability, formulation and lack of food safety processing with regards to addition to foods intended for human consumption. For example, the '203 publication does not describe any processing information with regard to repeatable production of the product. This could lead, for example, to poorly dispersed, undissolved or not hydrated ingredients, which in turn, can lead to a formulation that is not suitable for prevention of microbial growth or contamination. Further, lack of a 5-log kill step, for example, presents inherent risk to not only the probiotic composition of the '203 publication, but also to potential foods being dosed with the composition. Without a properly defined 5-log kill step, risk of microbial contamination, which may show dormancy in the inventions composition, will grow once added to food products that present optimal growth factors including water and food source. Having no defined kill step also presents the opportunity for background contamination through use of ingredients including corn syrup, prebiotics, and thickeners.

In light of the technical issues summarized above, one of the goals of the present disclosure was to provide an alimentary probiotic formulation and a processing method that is reproducible by those of ordinary skill in the art and avoids the disadvantages of the prior art and conventional compositions and methods, and guarantees a product that is safe and effective for human consumption.

SUMMARY OF THE DISCLOSURE

The disclosure provides for an improved delivery of spore-containing probiotic compositions that can retain their cellular viability under ambient, refrigerated, and frozen storage conditions over extended time periods and that can then be added to and remain stable in food and beverage products.

Accordingly, in certain embodiments, a method for preparing a shelf stable spore-containing probiotic alimentary additive, comprises providing a liquid slurry comprising spores from at least one spore-forming probiotic bacterial strain, a saccharide, and a humectant; and pasteurizing the liquid slurry to yield the alimentary additive, wherein the alimentary additive comprises a water activity (Aw) of less than about 0.7; the alimentary additive comprises a pH from about 2.0 to 9.5; and a plurality of the spores remain in an un-germinated state and remain uniformly suspended for at least two months after the pasteurizing step to yield a shelf stable spore-containing probiotic alimentary additive.

In certain embodiments, at least 90, 95, or 99% of the spores remain in an un-germinated state for at least two months after the pasteurizing step. In certain embodiments, at least 90, 95, 99% of the spores remain germination competent. In certain embodiments, at least 90, 95, 99% of the spores germinate following exposure to a germination-permissive condition.

In certain embodiments, at least 90, 95, or 99% of the spores germinate following ingestion by a mammal. In certain embodiments, the germination-permissive condition comprises at least 1 Aw and 37° C. In certain embodiments, at least 90% of the spores are viable after pasteurization.

In certain embodiments, the alimentary additive comprises less than 1% (w/v) of vegetative bacterial cells.

In certain embodiments, the at least one spore-forming probiotic bacterial strain comprises at least one *Bacillus* bacterial strain. In certain embodiments, the at least one spore-forming probiotic bacterial strain comprises at least one of *Bacillus coagulans* bacterial strain, at least one of *Bacillus subtilis* bacterial strain, at least one of *Bacillus clausii* bacterial strain, at least one of *Bacillus indicus* bacterial strain, at least one of *Bacillus licheniformis* bacterial strain, at least one of *Bacillus pumilus* bacterial strain, at least one of *Bacillus amyloliquifaciens* bacterial strain, or at least one of *Bacillus megaterium* bacterial strain. In certain embodiments, the at least one *Bacillus coagulans* bacterial strain comprises *Bacillus coagulans* GBI-30 strain (ATCC Designation Number PTA-6086).

In certain embodiments, a plurality of spores is present in the alimentary additive in an amount from about 500 million CFU/g to 1 trillion CFU/g by weight of the composition.

In certain embodiments, the at least one humectant is at least one of glycerin, a sugar, a salt, propylene glycol, or a gum.

In certain embodiments, the alimentary additive further comprises at least one rheology modifier that does not contain inulin, wherein the at least one rheology modifier is present in an amount from about 0.01% to 0.3% by weight of the composition. In certain embodiments, the at least one rheology modifier is at least one of xanthan gum, gum arabic, gellan gum, guar gum, or carrageenan.

The disclosure also provides for a spore-containing probiotic composition. In certain embodiments, a spore-containing probiotic composition comprises a liquid slurry comprising, a probiotic material comprising a plurality of spores from at least one spore-forming probiotic bacterial strain wherein at least 90% of the spores are viable at pasteurization times and temperatures; a saccharide, and at least one humectant, or combinations thereof, wherein the composition has a water activity (Aw) of less than about 0.7 and a pH of less than about 5.0.

The disclosure also provides for a food product, comprising the spore-containing probiotic composition.

The disclosure also provides a beverage product, comprising the spore-containing probiotic composition.

DETAILED DESCRIPTION

The compositions and methods described herein provide a solution to the drawbacks and limitations of existing probiotic products. Spore-containing (non-vegetative) probiotic compositions are provided that can survive specific time-temperature, pH, and water activity environments when pasteurized to deliver consistent microbiological viability, and subsequent activity when added to food and beverage products. For example, the probiotic viability of the spore-containing probiotic compositions can be from about 500 million (M) colony forming unit (CFU)/gram (g) to 1 trillion (T) colony forming unit (CFU)/gram (g) by weight of the composition after the pasteurization process.

The spore-containing probiotic compositions described herein can be in the form of a uniformly suspended and dispersible liquid slurry. The liquid slurry is designed such that it can remain stable in ambient storage conditions at least before being added to a food or beverage product (e.g., a refrigerated food or beverage product or a frozen food or beverage product or ambient food or ambient beverage). The liquid slurry form can be more easily and economically added to a food or beverage product as compared to a powdered form, e.g., lower processing time, less expensive to produce, manufacture, and process, and uniformly concentrated throughout the composition. As used herein, "food" refers to human food, pet food (e.g., food designed for consumption by companion animals such as dogs, cats, and the like), or animal feed (e.g., food designed for consumption by non-companion animals such as livestock and the like). As used herein, "beverage" refers a human beverage, a pet beverage (e.g., a beverage designed for consumption by companion animals such as dogs, cats, and the like), or animal beverage (e.g., a beverage designed for consumption by non-companion animals such as livestock and the like). Further, the liquid slurry is designed to withstand pasteurization methods, such as High Temperature Short Time (HTST), High Pressure Pasteurization (HPP), and the like. In some embodiments, the spore-containing probiotic compositions can have an extended shelf-life. For example, the extended shelf-life can be up to three months, up to six months, or up to the shelf-life of the food or beverage product. Further, the compositional makeup of the liquid slurry results in viscosity and rheological properties that allow the liquid slurry to be added to a food or beverage product using any suitable liquid delivery system (e.g., dosage systems).

The spore-containing probiotic compositions generally include a probiotic material. In some embodiments, the probiotic material present in the composition can be in an amount from about 5% to 70%, from about 30% to 70%, from about 40% to 60%, from about 40% to 50%, from about 5% to 30%, from about 5% to 25%, or from about 5% to 20% by weight of the composition. In other embodiments, the probiotic material can be present in the composition in an amount between any of these recited values.

The probiotic material includes a plurality of spores and at least one excipient as described below. The plurality of spores are from at least one spore-forming probiotic bacterial strain. In some embodiments, the plurality of spores present in the composition can be in an amount from about 500 million (M) CFU/g to 1 trillion (T) CFU/g, about 1 billion (B) CFU/g to 1 trillion (T) CFU/g, from about 500 million (M) CFU/g to 5 billion (B) CFU/g, or from about 500 million (M) CFU/g to 10 billion (B) CFU/g by weight of the composition. In other embodiments, the plurality of spores present in the composition can be in an amount between any of these recited values.

The at least one spore-forming bacterial strain can include any spore-forming bacterial strain(s). In some embodiments, the at least one spore-forming probiotic bacterial strain can be at least one *Bacillus* bacterial strain. Non-limiting examples of suitable spore-forming bacterial strains can include at least one of *Bacillus coagulans* bacterial strain, at least one of *Bacillus subtilis* bacterial strain, at least one of *Bacillus clausii* bacterial strain, at least one of *Bacillus indicus* bacterial strain, at least one of *Bacillus licheniformis* bacterial strain, at least one of *Bacillus pumilus* bacterial strain, at least one of *Bacillus amyloliquifaciens* bacterial strain, at least one of *Bacillus megaterium* bacterial strain, or any combinations thereof.

In some embodiments, the at least one spore-forming probiotic bacterial strain can be at least one *Bacillus coagulans* bacterial strain. For example, the at least one *Bacillus coagulans* bacterial strain can include *Bacillus coagulans* GBI-30 strain (ATCC Designation Number PTA-6086). Additional details of the *Bacillus coagulans* GBI-30 strain can be found in U.S. Pat. Nos. 6,849,256, 7,713,726, and 8,277,799, each of which is incorporated herein by reference in its entirety.

The homogeneity of the spore distribution throughout the spore-containing probiotic compositions can be stable. For example, the composition does not undergo substantial sedimentation (e.g., greater than 5% of the amount of spores by volume of the spore-containing probiotic compositions)

or phase separation (e.g., greater than 5% of the amount of spores by volume of the spore-containing probiotic composition). This homogeneity, alone or in combination with, the specific gravity of the spore-containing probiotic composition can facilitate reproducible dosing of the spore-containing probiotic composition into food or beverage products. In some embodiments, the specific gravity of the composition can be from about 1.0 to 1.5 or from about 1.25 to 1.45. In other embodiments, the specific gravity of the composition can be between any of these recited values.

In some embodiments, the probiotic material can also include at least one saccharide. Nonlimiting examples of suitable saccharides include monosaccharides and polysaccharides, such as inulin or maltodextrin, galactooseccharides, fructooligosaccharides. For example, the inulin can be present in an amount from about 75% to 95%, from about 80% to 90%, or from about 75% to 80% by weight of the probiotic material. In such embodiments, the inulin can function as a rheology modifier.

In other embodiments, the probiotic material does not include inulin. In such embodiments, inulin can be separately added to the spore-containing probiotic composition. As used herein, "added inulin" is used to refer to inulin that is not contained within the probiotic material, but rather separately added to the to the spore-containing probiotic composition. For example, in some embodiments, separately added inulin can be present in an amount from about 0.1% to 30%, from about 0.1% to 25%, or from about 0.1% to 20% by weight of the composition. In such instances, the separately added inulin can function as a rheology modifier.

In some embodiments, the probiotic material can include maltodextrin. In such embodiments, inulin can be separately added, referred to herein as "added inulin," to the spore-containing probiotic composition. For example, in some embodiments, added inulin can be present in an amount from about 0.1% to 30%, from about 0.1% to 25%, or from about 0.1% to 20% by weight of the composition.

In some embodiments, the probiotic material can include non-fat dry milk. In such embodiments, inulin can be separately added, referred to herein as "added inulin," to the spore-containing probiotic composition. For example, in some embodiments, separately added inulin can be present in an amount from about 0% to 30%, from about 0% to 25%, or from about 0% to 20% by weight of the composition.

In addition to probiotic material, the spore-containing probiotic compositions can include water. In some embodiments, water is present in an amount from about 20% to 60%, from about 20% to 50%, or from about 20% to 40% by weight of the composition.

Further, the dormancy of the spores of the spore-containing probiotic compositions can be maintained by minimizing the water activity, e.g., to less than about 0.95 water activity (Aw). That is, low water activity can inhibit germination of the spores. Low water activity also reduces sedimentation or phase separation within the compositions for a period of time, e.g., for about up to three months, up to six months, or up to the shelf-life of a food or beverage product containing the composition(s). As a result, the spore-containing probiotic compositions can remain uniformly suspended, prior to adding the compositions to a product, e.g., a food or beverage product. That is, unlike conventional spore-containing probiotic compositions, e.g., Enterogermina that is produced and marketed by Sanofi, the present spore-containing probiotic compositions can be added to a food product or beverage product without the need to thoroughly mix the compositions prior to addition to the food or beverage product. Thus, an advantage of the spore-containing probiotic compositions described herein is maintenance of uniform suspension for extended periods of time.

Moreover, the inhibition of spore germination via low water activity, can lead to other advantages. For example, prior to desired use, the spores can remain uniformly dispersed throughout the compositions for extended periods of time, and thereby increasing shelf-life. Further, the spores of the spore-containing probiotic compositions can remain in their resistant states such that they do not germinate or proliferate in response to environmental factors. As a result, the spores can survive post-pasteurization, such as High Temperature Short Time (HTST), High Pressure Pasteurization (HPP), and the like.

In some embodiments, the water activity of the spore-containing probiotic compositions can be from about 0.001 Aw to about 0.99 Aw. In some embodiments the water activity of the spore-containing probiotic compositions is less than or equal to about 0.95 Aw, or less than or equal to about 0.90 Aw, or less than or equal to about 0.85 Aw, or less than or equal to about 0.80 Aw, or less than or equal to about 0.75 Aw, or less than or equal to about 0.70 Aw, or less than or equal to about 0.65 Aw, or less than or equal to about 0.60 Aw, or less than or equal to about 0.55 Aw, or less than or equal to about 0.50 Aw, or less than or equal to about 0.45 Aw, or less than or equal to about 0.40 Aw, or less than or equal to about 0.35 Aw, or less than or equal to about 0.30 Aw, or less than or equal to about 0.25 Aw, or less than or equal to about 0.20 Aw, or less than or equal to about 0.15 Aw, or less than or equal to about 0.10 Aw, or less than or equal to about 0.05 Aw, or less than or equal to about 0.01 Aw, or less than or equal to about 0.005 Aw, or less than or equal to about 0.004 Aw, or less than or equal to about 0.003 Aw, or less than or equal to about 0.002 Aw. This parameter can be achieved by the inclusion of at least one humectant. For example, in some embodiments, the spore-containing probiotic composition can include at least one humectant. As used herein, a "humectant" is a hygroscopic substance, one that attracts and retains water. The at least one humectant can be glycerin. The glycerin can be in an amount from about 30% to 75%, from about 30% to 70%, from about 40% to 75%, from about 50% to 75%, from about 55% to 65%, from about 50% to 70%, from about 40% to 60%, or from about 40% to 50% by weight of the composition. Non-limiting examples of other suitable humectants can include sugars, e.g., sorbitol (e.g., from about 30% to 75% by weight of the composition), salts (e.g., from about 30% to 75% by weight of the composition), propylene glycol (e.g., from about 30% to 75% by weight of the composition), and gums, e.g., xanthan acacia gum (e.g., from about 10% to 30% by weight of the composition).

The spore-containing probiotic compositions can include at least one rheology modifier that does not contain inulin and/or added inulin. Non-limiting examples of suitable rheology modifiers that do not contain inulin and/or added inulin include xanthan gum, guar gum, gum arabic, carrageenan, gellan gum, and the like. In some embodiments, the at least one rheology modifier that does not contain inulin and/or added inulin is present in an amount from about 0.01% to 0.3% by weight of the composition. For example, in some embodiments, the at least one rheology modifier that does not contain inulin and/or added inulin is xanthan gum that is present an amount from about 0.01% to 0.3% by weight of the composition. In other embodiments, the at least one rheology modifier that does not contain inulin and/or added inulin is gum arabic that is present an amount from about 0.01% to 0.3% by weight of the composition. In other embodiments, the at least one rheology modifier that does not contain inulin and/or added inulin is gellan gum that is present in an amount from about 0.01% to 0.3% by weight of the composition.

In some embodiments, the spore-containing probiotic compositions do not contain salt. In other embodiments, the spore-containing probiotic composition can contain salt that is present in an amount that is less than about 10%, less than about 5%, less than about 1%, less than about 0.1%, less than about 0.01%, less than about 0.001%, or less than about 0.0001% by weight of the composition. Non-limiting examples of salt include table salt, e.g. NaCl, kosher salt, iodized salt, sea salt, Himalayan salt. Other salts include, for example, chloride salts of potassium, magnesium, calcium, ammonium.

In some embodiments, the spore-containing probiotic compositions can have a viscosity from about 25 centipoise (cP) to 2000 centipoise (cP) measured at a temperature of 4° C. For example, the viscosity of the spore-containing probiotic compositions can be from about 5 cP to 100,000 cP, from about 5 cP to 10,000 cP, or from about 5 cP to 50,000 cP measured at a temperature of 4° C.

The spore-containing probiotic compositions can also include additional elements, such as natural flavor(s), preservatives, acidulants, etc., and any combination thereof. For example, in some embodiments, the spore-containing probiotic compositions can include at least one natural flavor that is present in an amount from about 0% to 2% by weight of the composition. In some embodiments, the spore-containing probiotic compositions can include at least one preservative that is present in an amount from about 0% to 2% by weight of the composition. As used herein, "preservative," refers to an ingredient that inhibits the growth of undesirable microorganisms. Non-limiting examples of suitable preservatives include potassium sorbate, sodium benzoate, sorbic acid, benzoic acid, and propionic acid.

In some embodiments, the spore-containing probiotic compositions can include at least one acidulant that is present in an amount from about 0% to 2% by weight of the composition. As used herein, "acidulant," refers to an ingredient that lowers the pH of a composition to a final pH (e.g., below about 5). The at least one acidulant can be an organic or mineral acid. Non-limiting examples of suitable acidulants include lactic acid, acetic acid, citric acid, hydrochloric acid, malic acid, and phosphoric acid. The addition of at least one acidulant to the spore-containing probiotic compositions can modify the pH of the compositions so as to, for example, inhibit the growth of spoilage microorganisms. In some embodiments, the pH of the spore-containing probiotic compositions that include an acidulant (e.g., lactic acid), can have a pH of less than 4.6. For example, in some embodiments, the spore-containing probiotic compositions can have a pH from about 2.0 to 5, from about 2.5 to 5, or from about 3.0 to 5.

In some embodiments, the spore-containing probiotic compositions can have a pH from about 2.0 to 9.5, from about 3.0 to 8.0, or from about 2.5 to 8.5.

The spore-containing probiotic compositions can be produced using any suitable method. For example, in some embodiments, the method can include mixing water and glycerin together to form a first mixture, adding at least one rheology modifier to the probiotic material (e.g., at a 1:10 ratio) to form a second mixture, and then combining and mixing (e.g., under high shear) the first and second mixtures to form a liquid slurry. The method can also include adding at least one acidulant, e.g., lactic acid, or preservative, e.g., potassium sorbate, sodium benzoate, and/or sorbic acid. The method can also include, after the addition of at least one acidulant or preservative, homogenizing the liquid slurry under high shear. After homogenization, the liquid slurry can be pasteurized (e.g., via HPP or HTST), thereby forming a spore-containing probiotic composition and thereafter packaged (e.g., in a 0.1-20 L bag with or without a cap). Alternatively, after the addition of at least one acidulant or preservative, the step of homogenizing the liquid slurry under high shear, thereby produces the spore-containing probiotic composition, which can then be packaged. In some embodiments, the packaged the spore-containing probiotic composition can then be pasteurized (e.g., via HPP).

The packaged spore-containing probiotic composition can be added, for example, to a food or beverage product, e.g., via mixing, e.g., low or high agitation, or spraying. In some embodiment, the delivery of the packaged slurry into a food or beverage product can be carried under out under aseptic conditions.

A spore-containing probiotic liquid slurry composition can be an additive to a food or beverage product. The food or beverage product can be refrigerated, frozen, or ambient.

The spore-containing compositions and methods may be further understood with the following non-limiting examples.

EXAMPLES

Example 1: Preparation of Spore-Containing Probiotic Compositions

Sixteen different samples of spore-containing probiotic compositions were prepared using the exemplary procedure described below.

Water is heated or cooled in a jacketed stainless steel mixing vessel to 40° F.-100° F. The water is agitated with a high shear dissolver speed 20%-80% and side sweep agitation 50%-100%. During agitation, acidulant is added to the water until the pH is between 4.0-4.6. Optionally, a preservative is added. Xanthan gum and/or gum arabic and/or gellan gum is/are mixed with the spore-containing probiotic powder at approximately a 1:10 ratio. Dry matter is added to the water/acidulant and blended with a high shear dissolver speed 20%-80% and side sweep agitation 50%-100% to form a liquid slurry. This is mixed for 5 minutes. During agitation, glycerin at 40° F.-100° F. is added to the liquid slurry. The liquid slurry is mixed for 5-20 minutes using a high shear dissolver speed 20%-80% and side sweep agitation 50%-100%. The liquid slurry is transferred from the vessel and through inline high shear equipment (e.g., IKA, Greerco, GEA, Niro Soavi Homogenizer). The liquid slurry is then transferred from the shear equipment into and through heat treatment equipment (e.g., plate or scraped surface heat exchanger) to heat the liquid slurry to a temperature between 160° F.-200° F. for 15-45 seconds. The heated liquid slurry is then cooled to a temperature of 50° F. or less via inline cooling heat exchangers (plate or scraped surface). The cooled liquid slurry is then packaged into a container such as a 0.1 L-20 L bag-in-box.

The compositional makeup of samples 1-8 and 9-16 are shown in Table 1A and 1B, respectively.

TABLE 1A

Compositional Makeup of Samples 1-8

| | SAMPLE 1 Weight % | SAMPLE 2 Weight % | SAMPLE 3 Weight % | SAMPLE 4 Weight % | SAMPLE 5 Weight % | SAMPLE 6 Weight % | SAMPLE 7 Weight % | SAMPLE 8 Weight % |
|---|---|---|---|---|---|---|---|---|
| Water | 53.177 | 51.877 | 41.454 | 39.500 | | 27.500 | 29.450 | 29.400 |
| Glycerin | | | | 50.000 | 89.500 | 50.000 | 55.000 | 55.000 |
| Probiotic Material A (Spore-containing powder with 75-90% by wt. Inulin and 15 billion Spores) | 1.300 | 2.600 | 13.000 | 10.000 | 10.000 | 10.000 | 15.000 | 15.000 |
| Gum Arabic | 45.000 | 45.000 | 45.000 | | | 12.000 | | |
| Gellan Gum | 0.023 | 0.023 | 0.046 | | | | 0.050 | 0.100 |
| Natural Flavor | 0.500 | 0.500 | 0.500 | 0.500 | 0.500 | 0.500 | 0.500 | 0.500 |
| Total | 100.000 | 100.000 | 100.000 | 100.000 | 100.000 | 100.000 | 100.000 | 100.000 |

TABLE 1B

Compositional Makeup of Samples 9-16

| | SAMPLE 9 Weight % | SAMPLE 10 Weight % | SAMPLE 11 Weight % | SAMPLE 12 Weight % | SAMPLE 13 Weight % | SAMPLE 14 Weight % | SAMPLE 15 Weight % | SAMPLE 16 Weight % |
|---|---|---|---|---|---|---|---|---|
| Water | 29.350 | 29.500 | 25.890 | 28.520 | 29.500 | 27.650 | 27.650 | 27.650 |
| Glycerin | 55.000 | 54.455 | 43.000 | 50.200 | 54.465 | 46.000 | 46.000 | 46.000 |
| Probiotic Material A (Spore-containing powder with 75-90% by wt. Inulin and 15 billion Spores) | 15.000 | 15.000 | 30.000 | | 15.000 | 25.000 | 25.000 | 25.000 |
| Probiotic B (Maltodextrin and 75 billion spores) | | | | 15.000 | | | | |
| Xanthan Gum | | 0.045 | 0.010 | 0.080 | 0.035 | 0.050 | 0.050 | 0.050 |
| Gellan Gum | 0.150 | | | | | | | |
| Inulin-added | | | | 5.000 | | | | |
| Natural Flavor | 0.500 | 0.500 | 0.500 | 0.500 | 0.500 | 0.500 | 0.500 | 0.500 |
| Potassium Sorbate | | | | | | 0.100 | | |
| Sodium Benzoate | | | | | | | 0.100 | |
| Sorbic Acid | | | | | | | | 0.100 |
| Lactic Acid | | 0.500 | 0.600 | 0.700 | 0.500 | 0.700 | 0.700 | 0.700 |
| Total | 100.000 | 100.000 | 100.000 | 100.000 | 100.000 | 100.000 | 100.000 | 100.000 |

Example 2: Characterization of Spore-Containing Compositions

Samples 1-16 as prepared in Example 1 were each characterized. Table 2 shows the various analyses performed and the methods used. Table 3A shows the results of these analyses for Samples 1-8 and Table 3B shows the results of these analyses for Samples 9-16.

TABLE 2

| Analysis Performed | |
|---|---|
| Analysis | Method of Determination/Instrumentation |
| Water Activity | A sample was transferred into a disposable sample cup, completely covering the bottom of the cup, if possible. The disposable sample cup was then placed into an Aqua Lab Tuneable Diode Laser Water Activity Meter for analysis. The Aqua Lab reading cycle continues until the rate of change of three consecutive readings are less than 0.0005 $A_w$ of each other. When the Aqua Lab Tuneable Diode Laser Water Activity Meter has finished its read cycle, the water activity and read is displayed. |
| pH | Thermo Scientific Orion series benchtop pH probe was used to determine the pH of a sample. |
| Sedimentation | A 1000 mL of a sample was transferred into a 1000 mL plastic clear container and stored at a temperature of 19° C.-23° C. After 24 hours, the sample was visually assessed for sedimentation. |

TABLE 2-continued

| Analysis Performed | |
|---|---|
| Phase Separation | A 1000 mL of a sample was transferred in a 1000 mL plastic clear container and stored at a temperature of 19° C.-23° C. After 24 hours, the sample was visually assessed for phase separation. |
| Particle Size | A sample was dispersed in dispersant and placed into a Malvern Mastersizer 3000 Laser Diffraction Instrument. Analysis was performed on a sample using Mastersizer software v.3.62. The analysis was carried out under the following testing parameters: |

| Dispersant properties | |
|---|---|
| Dispersant name | Water |
| Refractive index | 1.000 |
| Level sensor threshold | 100.000 |

| Measurement duration | |
|---|---|
| Background measurement duration (red) | 10.00 s |
| Sample measurement duration (red) | 10.00 s |
| Perform blue light measurement? | Yes |
| Background measurement duration (blue) | 10.00 s |
| Sample measurement duration (blue) | 10.00 s |
| Assess light background stability | No |

| Measurement sequence | |
|---|---|
| Aliquots | 1 |
| Automatic number of measurements | No |
| Pre-alignment delay | 0.00 s |
| Number of measurements | 5 |
| Delay between measurements | 0.00 s |
| Pre-measurement delay | 0.00 s |
| Close measurement window after measurement | No |

| Measurement obscuration settings | |
|---|---|
| Auto start measurement | No |
| Obscuration low limit | 0.10% |
| Obscuration high limit | 20.00% |
| Enable obscuration filtering | No |

| Measurement alarms | |
|---|---|
| Use Background Check | No |
| Background Check Limits | [1, 200], [20, 60] |

| Accessory control settings | |
|---|---|
| Accessory name | Hydro MV |
| Is accessory dry? | No |
| Stirrer speed | 2400 rpm |
| Ultrasound percentage | 0% |
| Fill Dispersant Source Identifier | Auto |
| Manual tank fill? | No |
| Degas after tank and cell fill | Yes |
| Sonicate to stability? | No |
| Ultrasound mode | Pre-Measurement |
| Degas after pre-measurement ultrasound | No |
| Align after pre-measurement ultrasound | No |
| Ultrasonication duration | 10.00 s |

TABLE 2-continued

| Analysis Performed | |
|---|---|

| Clean sequence settings | |
|---|---|
| Clean sequence type | Normal |
| Sonicate during clean? | Yes |
| Manually Fill Tank During Clean? | No |
| Clean Dispersant Source Identifier | Auto |
| Clean Dispersant Level Sensor Threshold | 0 |
| Degas After Clean? | No |

| Analysis settings | |
|---|---|
| Analysis model | General Purpose |
| Single result mode | No |
| Number of killed inner detectors | 0 |
| Blue light detectors killed | No |
| Fine powder mode | No |
| Analysis sensitivity | Normal |
| Analysed as Mastersizer 3000E? | No |

| Result Settings | |
|---|---|
| Result range is limited | Yes |
| Low size | 0.020 µm |
| High Size | 2000.000 µm |
| Result Units | Volume |
| Extend Result | No |
| Result Emulation | No |

| | |
|---|---|
| Viscosity | A 500 mL sample was transferred into a 600 mL container. Viscosity was then measured on a Brookfield RV Viscometer using Spindle No. 3 at 50 rpm at 4° C. After 30 seconds of rotation, the reading was taken. |
| Probiotic Viability - Live and Active Microbiological Counts. | Microbiological enumeration according to the Food Chemical Codex (FCC) 10 method (Food Chemical Codex FCC10 First Supplement. Monograph/*Bacillus coagulans* GBI-30,6086/3781. Published by United States Pharmacopeia., 2017). |
| Taste | A taste assessor was served a gold standard sample deemed to have the appropriate level of sweetness, sourness and taste profile. The taste assessor was then served a sample and compared the sample to the gold standard sample to determine whether the sample has acceptable levels of sweet and sour, and without off flavors. |
| Specific Gravity | Mettler Toledo DA100 Density Meter was used to determine the specific gravity/density of a sample |

TABLE 3A

Results of analyses listed in Table 2.

| | SAMPLE 1 | SAMPLE 2 | SAMPLE 3 | SAMPLE 4 | SAMPLE 5 | SAMPLE 6 | SAMPLE 7 | SAMPLE 8 |
|---|---|---|---|---|---|---|---|---|
| Water Activity | 0.6-0.7 | 0.6-0.7 | 0.6-0.7 | 0.6-0.7 | 0.6-0.7 | 0.6-0.7 | 0.6-0.7 | 0.6-0.7 |
| pH | 4.0-8.0 | 4.0-8.0 | 4.0-8.0 | 4.0-8.0 | 4.0-8.0 | 4.0-8.0 | 4.0-8.0 | 4.0-8.0 |
| Sedimentation | 10% | 10% | 10% | 20% | 10% | 10% | 10% | 10% |
| Phase Separation | N/A | N/A | N/A | N/A | N/A | N/A | N/A | N/A |
| Particle Size (μm) | 1-1,000 | 1-1,000 | 1-1,000 | 1-1,000 | 1-1,000 | 1-1,000 | 1-1,000 | 1-1,000 |
| Viscosity (cP) | 1,000-100,000 | 1,000-100,000 | 1,000-100,000 | 1-100 | 100-10,000 | 100-10,000 | 1-1,000 | 1-1,000 |
| Probiotic Viability - Live and Active Microbiological Counts. (CFU/g by weight of the composition) | 1M-1B | 1M-1B | 500M-10B | 500M-10B | 500M-10B | 500M-10B | 500M-10B | 500M-10B |
| Taste | Conforms | Conforms | Conforms | Conforms | Conforms | Conforms | Conforms | Conforms |
| Specific Gravity | 1.0-1.5 | 1.0-1.5 | 1.0-1.5 | 1.0-1.5 | 1.0-1.5 | 1.0-1.5 | 1.0-1.5 | 1.0-1.5 |

TABLE 3B

Results of analyses listed in Table 2.

| | SAMPLE 9 | SAMPLE 10 | SAMPLE 11 | SAMPLE 12 | SAMPLE 13 | SAMPLE 14 | SAMPLE 15 | SAMPLE 16 |
|---|---|---|---|---|---|---|---|---|
| Water Activity | 0.6-0.7 | 0.6-0.7 | 0.6818 | 0.6-0.7 | 0.6-0.7 | 0.6-0.7 | 0.6-0.7 | 0.6-0.7 |
| pH | 4.0-8.0 | <4.6 | 4.27 | <4.6 | <4.6 | <4.6 | <4.6 | <4.6 |
| Sedimentation | 10% | N/A | N/A | N/A | N/A | N/A | N/A | N/A |
| Phase Separation | N/A | N/A | N/A | N/A | N/A | 50% | 50% | N/A |
| Particle Size (μm) | 1-1,000 | 1-1,000 | 8.346 | 1-1,000 | 1-1,000 | 1-1,000 | 1-1,000 | 1-1,000 |
| Viscosity (cP) | 1-1,000 | 1-1,000 | 992 | 1-1,000 | 1-1,000 | 100-10,000 | 100-10,000 | 100-10,000 |
| Probiotic Viability - Live and Active Micro. (CFU/g by weight of the composition) | 500M-10B | 500M-10B | 4.35B | 500M-10B | 500M-10B | 500M-10B | 500M-10B | 500M-10B |
| Taste | Conforms | Conforms | Conforms | Conforms | Conforms | Conforms | Conforms | Conforms |
| Specific Gravity | 1.0-1.5 | 1.0-1.5 | 1.33 | 1.0-1.5 | 1.0-1.5 | 1.0-1.5 | 1.0-1.5 | 1.0-1.5 |

Example 3: Comparative Testing—Sedimentation

The liquid compositions were stored for two weeks without agitation. The liquid compositions were visually inspected, and it was found that the components of the liquid compositions did not sediment.

Example 4: Comparative Testing—Water Activity and Viscosity

The Enterogermina samples (US 2015/0118203) were tested for water activity and viscosity and compared to the samples herein. The Aw of the Enterogermina product was equal to 1. In contrast, the Aw of Samples 1-16 herein is between about 0.6 to about 0.7.

Definitions

The terminology used herein is for the purpose of describing particular embodiments only and is not intended to be limiting of the present disclosure. Unless specifically defined otherwise, all technical and scientific terms used herein shall be taken to have the same meaning as commonly understood by one of ordinary skill in the art (e.g., in cell culture, bacteriology, molecular genetics, and biochemistry).

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used in this specification and the appended claims, the term "or" is generally employed in its sense including "and/or" unless the content clearly dictates otherwise.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

As used herein, the term "germination-permissive conditions" are environmental conditions which allow for the germination of the spores. These environmental conditions include temperature, nutrients, pH levels and the like.

As used herein, "shelf-stable" refers to a composition that is stable under ambient, refrigerated or frozen conditions and safe for consumption.

As used herein an "alimentary additive" is a solid and/or fluid nutrient additive intended for human or animal consumption.

No limit is placed on the manner in which the shelf stable spore-containing probiotic alimentary additive described herein is marketed, sold, distributed, stored, etc. For example, the examples above describe embodiments where the spore-containing probiotic compositions are packaged in various formats, such as in a bag with or without a cap and in a bag-in-box. The shelf stable spore-containing probiotic alimentary additive can be distributed in these or similar formats for industrial processing for food and beverage applications. The shelf stable spore-containing probiotic alimentary additive can also be packaged and distributed for individual consumer consumption, such as for a dietary supplement. This may include any well-known single serving and multi-serving packaging, including sealed vials, liquid supplements, etc.

While the above description may have focused on the use of a spore-forming probiotic bacterial strain and on conditions for maintaining dormancy, it will be understood that the shelf stable spore-containing probiotic alimentary additive could also be prepared using (separate to the spores or in addition to the spores) encapsulated (non-sporulating) vegetative probiotics, such as, for example, those of *Lactobacillus* and *Bifidobacterium* species.

One skilled in the art will appreciate further features and advantages of the present disclosure based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A spore-containing probiotic composition, comprising:
    a pasteurized liquid slurry comprising,
    a probiotic material comprising spores from at least one spore-forming probiotic bacterial strain wherein at least 90% of the spores are viable at pasteurization times and temperatures;
    a saccharide, and
    at least one humectant,
    wherein the composition has a water activity (Aw) of less than about 0.7, and a pH of about 8.0 or less.

2. The composition of claim 1, wherein the at least one humectant is at least one of glycerin, a sugar, a salt, propylene glycol, or a gum.

3. The composition of claim 1, wherein the at least one spore-forming probiotic bacterial strain comprises at least one *Bacillus* bacterial strain.

4. The composition of claim 3, wherein the at least one spore-forming probiotic bacterial strain comprises at least one of *Bacillus coagulans* bacterial strain, at least one of *Bacillus subtilis* bacterial strain, at least one of *Bacillus clausii* bacterial strain, at least one of *Bacillus indicus* bacterial strain, at least one of *Bacillus licheniformis* bacterial strain, at least one of *Bacillus pumilus* bacterial strain, at least one of *Bacillus amyloliquifaciens* bacterial strain, or at least one of *Bacillus megaterium* bacterial strain.

5. The composition of claim 3, wherein the at least one *Bacillus coagulans* bacterial strain comprises *Bacillus coagulans* GBI-30 strain (ATCC Designation Number PTA-6086).

6. The composition of claim 1, wherein the plurality of spores is present in the composition in an amount from about 500 million CFU/g to 1 trillion CFU/g by weight of the composition.

7. The composition of claim 1, further comprising at least one rheology modifier that does not contain inulin, wherein the at least one rheology modifier is present in an amount from about 0.01% to 0.3% by weight of the composition.

8. The composition of claim 7, wherein the at least one rheology modifier is at least one of xanthan gum, gum arabic, gellan gum, guar gum, or carrageenan.

9. A food product, comprising:
    a food, and
    the spore-containing probiotic composition of claim 1.

10. A beverage product, comprising:
    a liquid beverage, and
    the spore-containing probiotic composition of claim 1.

11. A spore-containing probiotic composition, comprising:
    a liquid slurry comprising,
    a probiotic material comprising spores from *Bacillus coagulans* GBI-30 strain (ATCC Designation Number PTA-6086),
    wherein at least 90% of the spores are viable at pasteurization times and temperatures;
    a saccharide,
    at least one humectant,
    wherein the composition has a water activity (Aw) of less than about 0.7, and a pH of about 8.0 or less.

12. The composition of claim 1, wherein the at least one humectant is glycerin and the at least one rheology modifier is xanthan gum, gellan gum or a combination thereof.

13. The composition of claim 12, wherein glycerin is present in an amount of from 43% to 55% by weight of the composition, and wherein xanthan gum, gellan gum or a combination thereof is present in an amount of from 0.01% to 0.10% by weight of the composition.

14. The composition of claim 1, wherein the pH of the composition is about 2.0 to about 8.0.

15. The composition of claim 11, wherein the pH of the composition is about 2.0 to about 8.0.

16. The composition of claim 1, wherein the pH of the composition is less than about 5.0.

17. The composition of claim 11, wherein the pH of the composition is less than about 5.0.

\* \* \* \* \*